(12) United States Patent
Choi

(10) Patent No.: US 10,739,296 B2
(45) Date of Patent: Aug. 11, 2020

(54) TEST STRIP PROVIDING CODE SEQUENCE TO BE AUTOMATICALLY RECOGNIZED, AND BIOLOGICAL ANALYTE MONITORING DEVICE

(71) Applicant: PHILOSYS CO., LTD., Jeollabuk-do (KR)

(72) Inventor: In Hwan Choi, Jeollabuk-do (KR)

(73) Assignee: PHILOSYS CO., LTD., Jeollabuk-Do (KR)

( * ) Notice: Subject to any disclaimer, the term of this patent is extended or adjusted under 35 U.S.C. 154(b) by 12 days.

(21) Appl. No.: 15/977,014

(22) Filed: May 11, 2018

(65) Prior Publication Data
US 2018/0340907 A1 Nov. 29, 2018

(30) Foreign Application Priority Data

May 24, 2017 (KR) .......................... 10-2017-0064048
Apr. 6, 2018 (KR) .......................... 10-2018-0040425

(51) Int. Cl.
*C12Q 1/00* (2006.01)
*G01N 27/327* (2006.01)
(Continued)

(52) U.S. Cl.
CPC .......... *G01N 27/327* (2013.01); *B01L 3/5023* (2013.01); *C12Q 1/001* (2013.01); *G01N 33/48771* (2013.01); *G01N 33/5438* (2013.01); *G01N 33/558* (2013.01); *G01N 35/00732* (2013.01); *B01L 2300/0645* (2013.01);
(Continued)

(58) Field of Classification Search
CPC .................. G01N 33/48771; B01L 2300/0825
See application file for complete search history.

(56) References Cited

U.S. PATENT DOCUMENTS 6,827,829 B2 * 12/2004 Kawanaka ............. C12Q 1/006
204/403.02
2009/0125268 A1 5/2009 Perry
(Continued)

FOREIGN PATENT DOCUMENTS

KR 20090123395 A 12/2009
KR 20110025262 A 3/2011
(Continued)

OTHER PUBLICATIONS

English Translation of KR101489600 (Year: 2015).*

*Primary Examiner* — Luan V Van
*Assistant Examiner* — Caitlyn Mingyun Sun

(57) ABSTRACT

Disclosed is a biological analyte monitoring device including a strip inserter in which a test strip is to be inserted, and a processor configured to read a code sequence based on an element detected from an index region, a first code region, and a second code region of the test strip in response to the test strip being inserted in the strip inserter, wherein the processor is further configured to determine a target interval in which an index element formed in the index region is detected while the test strip is being inserted in the strip inserter, detect a first code element formed in the first code region in the target interval and detect a second code element formed in the second code region in the target interval, and identify the code sequence based on a result of detecting the first code element and the second code element.

10 Claims, 16 Drawing Sheets

(51) Int. Cl.
  *G01N 35/00*   (2006.01)
  *G01N 33/487*  (2006.01)
  *B01L 3/00*    (2006.01)
  *G01N 33/543*  (2006.01)
  *G01N 33/558*  (2006.01)

(52) U.S. Cl.
  CPC .. *B01L 2300/0825* (2013.01); *G01N 27/3271* (2013.01); *G01N 2035/00772* (2013.01)

(56) References Cited

U.S. PATENT DOCUMENTS

| | | |
|---|---|---|
| 2010/0255567 A1 | 10/2010 | Lieber et al. |
| 2013/0177479 A1 | 7/2013 | Morita et al. |
| 2013/0274581 A1* | 10/2013 | Choi .................. A61B 5/14532 600/365 |
| 2014/0206972 A1 | 7/2014 | Hayter et al. |
| 2017/0074856 A1 | 3/2017 | Gofman |

FOREIGN PATENT DOCUMENTS

| | | |
|---|---|---|
| KR | 20110095638 A | 8/2011 |
| KR | 101489600 B1 | 2/2015 |
| RU | 140764 U1 | 5/2014 |
| RU | 2553387 C2 | 6/2015 |
| RU | 2014139824 A | 4/2016 |
| WO | 2011027979 A2 | 3/2011 |

\* cited by examiner

TEST STRIP PROVIDING CODE SEQUENCE TO BE AUTOMATICALLY RECOGNIZED, AND BIOLOGICAL ANALYTE MONITORING DEVICE

CROSS-REFERENCE TO RELATED APPLICATION(S)

This application claims the priority benefit of Korean Patent Application No. 10-2017-0064048 filed on May 24, 2017, and Korean Patent Application No. 10-2018-0040425 filed on Apr. 6, 2018, in the Korean Intellectual Property Office, the disclosures of which are incorporated herein by reference for all purposes.

BACKGROUND

1. Field

One or more example embodiments relate to a test strip configured to provide a code sequence to be automatically recognized by a biological analyte monitoring device, and the biological analyte monitoring device configured to automatically recognize the code sequence from the test strip.

2. Description of Related Art

A biosensor may be classified as one of various types of sensors, for example, an enzyme sensor, a microbial sensor, an immunosensor, an organelle sensor, and a tissue membrane sensor, based on a type of biological analyte, and also broadly as an optical biosensor and an electrochemical biosensor based on a method of quantitatively analyzing a target substance in a biological sample.

The electrochemical biosensor may measure an electrical signal obtained from a reaction and a concentration of a target substance. The electrochemical biosensor may amplify a signal based solely on an extremely small sample and be reduced in size. In addition, the electrochemical biosensor may stably obtain a measured signal and be readily integrated with or be compatible with information technology (IT) equipment, such as, for example, a data communication device. The electrochemical biosensor may be provided in a structure in which an enzyme and a control agent are fixed to a cell composed of a reference electrode and an operating electrode. For example, when a sample is applied to the biosensor, a target substance in the sample is oxidized by a catalytic action of the enzyme and concurrently oxygen or an electron transport medium is reduced. The reduced oxygen or electron transport medium is forced to be oxidized by a voltage of an electrode, which induces a change in electron. By quantifying such a change in electron, the electrochemical biosensor may thus measure an amount of the target substance directly or indirectly.

The electrochemical biosensor may include, for example, a blood glucose strip. The blood glucose strip may be provided in a form of a panel that may absorb collected blood, and used to measure a blood glucose level, or a concentration of sugar in blood, after being inserted in a blood glucose monitor. The number of overweight or obese people is growing due to a relatively recent shift to a high-calorie and high-fat diet and a lack of exercise. In addition, the number of people suffering from diabetes is rapidly increasing and, due to medical advances, the number of elderly people is also increasing. Meanwhile, the level of health consciousness is on the rise. There is thus a growing demand for a blood glucose strip that may measure blood glucose more accurately.

SUMMARY

According to an aspect, there is provided a biological analyte monitoring device including a strip inserter in which a test strip is to be inserted and a processor configured to, in response to the test strip being inserted in the strip inserter, read a code sequence based on an element detected from an index region, a first code region, and a second code region of the test strip. The processor may be further configured to determine a target interval in which an index element formed in the index region is detected while the test strip is being inserted in the strip inserter, detect a first code element formed in the first code region in the target interval and detect a second code element formed in the second code region in the target interval, and identify the code sequence based on a result of detecting the first code element and the second code element.

The processor may be further configured to determine a code in the code sequence corresponding to the first code region in the target interval to be 1 in response to the first code element being detected from the first code region during the target interval, determine a code in the code sequence corresponding to the first code region in the target interval to be 0 in response to the first code element not being detected from the first code region during the target interval, determine a code in the code sequence corresponding to the second code region in the target interval to be 1 in response to the second code element being detected from the second code region during the target interval, and determine a code in the code sequence corresponding to the second code region in the target interval to be 0 in response to the second code element not being detected from the second code region during the target interval.

The processor may be further configured to allocate a first bit position to a code identified from the first code region and allocate a second bit position different from the first bit position to a code identified from the second code region.

The processor may be further configured to determine a plurality of target intervals in sequential order while the test strip is being inserted in the strip inserter, identify a plurality of first codes corresponding to the first code region in the respective target intervals, identify a plurality of second codes corresponding to the second code region in the respective target intervals, and allocate, to the second codes, a bit position different from a bit position allocated to the first codes.

In response to m index elements being detected, the processor may be further configured to determine m target intervals in sequential order, allocate 2m–1th through mth bit positions to the second code region, and allocate m–1th through 0th bit positions to the first code region.

The processor may be further configured to apply a signal to the second code element in response to a contact between the second code element and the strip inserter being detected, and detect a code element from the first code region and the second code region after an entry into the target interval.

The test strip may further include a reference region and a guide region. The processor may be further configured to determine a processing interval in which a reference element formed in the reference region and a guide element formed in the guide region are connected, determine, to be the target interval, an interval in which the index element connected to the reference element and the guide element is detected in the processing interval, determine that the first code element is formed in the first code region in response to a signal path from the first code region to the reference region being detected during the target interval, and determine that the second code element is formed in the second code region in response to a signal path from the second code region to the reference region being detected during the target interval.

The processor may be further configured to apply a signal to the first code element in response to a contact between the strip inserter and the first code element being detected in the target interval, determine that the first code element is formed in response to the applied signal reaching the reference element, apply a signal to the second code element in response to a contact between the strip inserter and the second code element being detected in the target interval, and determine that the second code element is formed in response to the applied signal reaching the reference element.

In response to the connection between the reference element and the guide element being released, the processor may be further configured to terminate the reading of the code sequence.

In response to a connection between the second code element and the reference element being detected after the connection between the reference element and the guide element is released, the processor may be further configured to determine that the inserting of the test strip is completed.

According to another aspect, there is provided a test strip including a base film, an electrode portion disposed on one surface of the base film, and a layer of which one surface is applied with an enzyme substance and formed on at least a portion of a top surface of the electrode portion to collect a biological analyte. The electrode portion may include a reference element elongatedly formed in an insertion direction in which the test strip is inserted in a biological analyte monitoring device, a plurality of first element regions disposed separately from each other along the insertion direction, a plurality of second element regions disposed separately from each other along the insertion direction, and a plurality of index elements disposed separately from each other along the insertion direction. Each of the index elements may overlap at least a portion of a first element region corresponding to a corresponding index element among the first element regions, and at least a portion of a second element region corresponding to a corresponding index element among the second element regions, in a direction vertical to the insertion direction.

The test strip may further include a guide element disposed in parallel with the reference element in the insertion direction and configured to indicate a processing interval for a code sequence indicating information associated with the test strip.

A front end of the reference element may be disposed ahead of a front end of the guide element in the insertion direction.

Based on the code sequence, a code element may be formed or not be formed in each of the first element regions and the second element regions.

A front end of each of the second element regions may be disposed ahead of a front end of a corresponding index element among the index elements in the insertion direction.

A front end of each of the first element regions may be disposed ahead of a front end of a corresponding index element among the index elements in the insertion direction.

The test strip may further include a guide element disposed in parallel with the reference element in the insertion direction. At least a portion of the reference element, at least a portion of the index elements, and at least a portion of the guide element may overlap to be connected in the direction vertical to the insertion direction.

The test strip may further include an insertion completion indicator disposed separately from the second element regions in the insertion direction, and disposed by being disconnected from the guide element indicating the processing interval for the code sequence, and disposed in a second code region including the second element regions.

The first element regions may indicate a code corresponding to a first bit position, and the second element regions may indicate a code corresponding to a second bit position different from the first bit position.

When a number of the index elements is m, the second element regions may indicate 2m–1th through mth bit positions in the code sequence based on an order in which each of the second element regions comes into contact with the biological analyte monitoring device while the test strip is being inserted in the biological analyte monitoring device, and the first element regions may indicate m–1th through 0th bit positions in the code sequence based on an order in which each of the first element regions comes into contact with the biological analyte monitoring device while the test strip is being inserted in the biological analyte monitoring device.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which.

DETAILED DESCRIPTION

Figure 1:
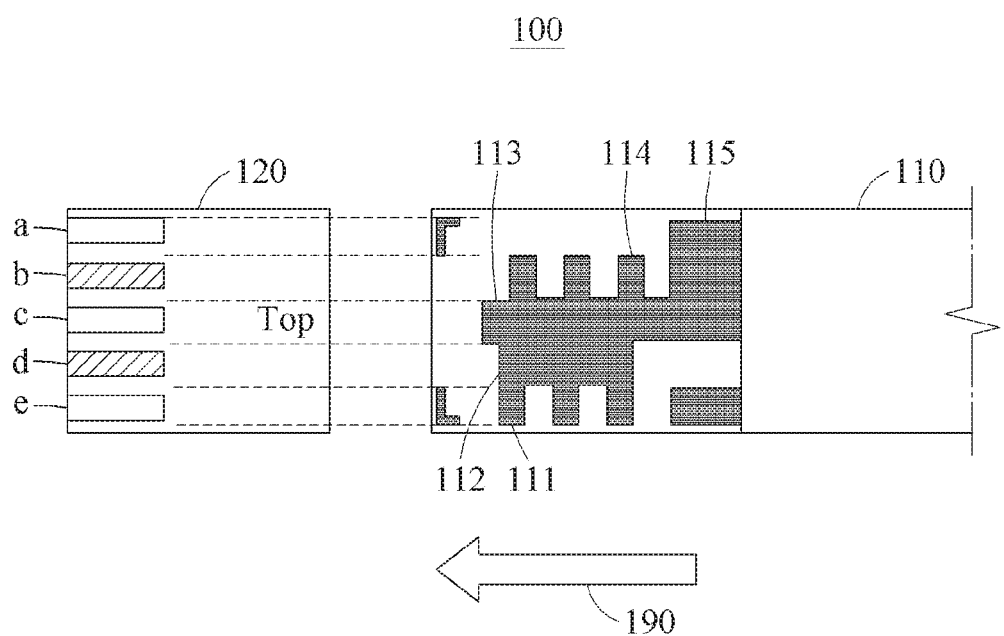
FIG. 1 is a diagram illustrating an example of a configuration of a biological analyte monitoring system according to an example embodiment.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for describing various examples only and is not to be used to limit the disclosure. As used herein, the articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Although terms such as "first," "second," "third," A, B, (a), (b), and the like may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing. As used herein, the term "and/or" includes any one and any combination of any two or more of the associated listed items.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Examples described herein may be embodied by various types of products, such as, for example, a personal computer (PC), a laptop computer, a tablet PC, a smartphone, a television (TV), a smart home appliance, an intelligent vehicle, a kiosk, a wearable device, and the like. For example, the examples may be applied to user verification or authentication in, for example, a smartphone, a mobile device, a smart home system, and the like. The examples may also be applied to payment services through the user verification or authentication. Further, the examples may also be applied to an intelligent vehicle system that is automatically started through the user verification or authentication. Hereinafter, the examples will be described in detail with reference to the accompanying drawings. Regarding the reference numerals assigned to the elements in the drawings, it should be noted that the same elements will be designated by the same reference numerals, wherever possible, even though they are shown in different drawings.

FIG. 1 is a diagram illustrating an example of a configuration of a biological analyte monitoring system according to an example embodiment.

Referring to FIG. 1, a biological analyte monitoring system 100, or a system for monitoring or measuring a biological analyte, includes a test strip 110 and a biological analyte monitoring device, or a device for monitoring or measuring a biological analyte. The biological analyte monitoring system 100 may also be referred to as a biosensor. The biological analyte monitoring system 100 may output an amount of a target biological analyte.

Herein, the term "biological analyte" refers to a material or substance associated with a living body, and to an analyte, for example, blood glucose as used herein. However, examples are not limited to the example described in the foregoing.

The test strip 110 refers to a strip configured to convert a biological analyte to a signal. The test strip 110 may be, for example, a transducer configured to convert a biological analyte to an electrical signal corresponding to an amount of the biological analyte in response to a reaction to the biological analyte. The test scrip 110 may include, for example, a blood glucose strip. The blood glucose strip refers to a chemically prepared test sheet that absorbs blood therein and may include an enzyme that reacts to blood sugar to cause an electrochemical reaction. The blood glucose strip will be described hereinafter as an example of the test strip 110. However, examples of the test strip 110 are not limited to the blood glucose strip.

Referring to the example illustrated in FIG. 1, the test strip 110 includes an electrode portion formed on one surface of the test strip 110. The electrode portion includes a reactor and a code indicator. A form of the electrode portion in the test strip 110, for example, a form of the code indicator, may indicate a code sequence. For example, as illustrated, the test strip 110 is inserted in a strip inserter 120 of the biological analyte monitoring device in an insertion direction 190, and the biological analyte monitoring device, for example, a blood glucose monitor, may automatically recognize the code sequence based on the form of the code indicator. The strip inserter 120 may include at least one pin to be in contact with the code indicator of the test strip 110, for example, five pins a, b, c, d, and e as illustrated in FIG. 1.

The code sequence used herein refers to a sequence including a series of codes. A code may indicate a bit value of 0 or a bit value of 1. For example, when the code sequence includes n codes, the code sequence may indicate n bits. In this example, when n is 3 and the n codes indicate 1, 1, and 0, respectively, the code sequence may indicate a binary value of 110. The binary value 110 may be decimally represented as $2^2+2^1+2^0=6$, wherein n denotes an integer greater than or equal to 1.

The code sequence of the test strip 110 may indicate test-related information. The test-related information may indicate, for example, a type of biological analyte which is an analysis target of the Lest strip 110. For example, the code sequence may indicate blood glucose as the analysis target of the test strip 110. However, examples are not limited to the example described in the foregoing, and the test-related information may indicate a correction value to compensate for an error that may be caused from a characteristic of the test strip 110.

For example, an error may occur in a signal indicated by the test strip 110 reacting to the biological analyte due to a process, a raw material, or an environmental factor. The biological analyte monitoring device may automatically recognize, from the code indicator of the test strip 110, the code sequence indicating such a correction value that compensates for such an error. The biological analyte monitoring device may correct a measurement result obtained through the test strip 110 using the correction value corresponding to the recognized code sequence. The biological analyte monitoring device may store a list of correction values through a memory. For example, the biological analyte monitoring device may store the list of correction values by arranging them. The biological analyte monitoring device may load, from the list, a correction value corresponding to the code sequence that is automatically recognized.

The reactor may react to the biological analyte to generate a signal. For example, the reactor may react to the biological analyte to generate an electrical signal corresponding to an amount of the biological analyte.

The code indicator may indicate the code sequence as described above. For example, the form of the code indicator may be automatically recognized by the biological analyte monitoring device when the test strip 110 is inserted in the biological analyte monitoring device, and the form of the code indicator may indicate the code sequence. In addition, the code indicator is connected to the reactor, and the code indicator may thus transmit, to the biological analyte monitoring device, the electrical signal corresponding to the amount of the biological analyte generated by the reactor when the test strip 110 is inserted in the biological analyte monitoring device.

As illustrated, the code indicator includes a first code element 111, a guide element 112, a reference element 113, an index element 114, and a second code element 115.

The first code element 111 may indicate a code corresponding to at least a portion of the code sequence. For example, when the first code element 111 is formed in a target interval defined by the index element 114, the first code element 111 may indicate a bit value of 1. Conversely, when the first code element 111 is not formed in the target interval or the first code element 111 is not connected to the index element 114, a bit value of a first code region in the target interval may indicate 0. The first code region will be described in detail with reference to FIG. 4.

The guide element 112 may indicate an interval in which information needs to be processed by the biological analyte monitoring device. For example, the guide element 112 may indicate a processing interval in which codes included in the code sequence indicating the information associated with the test strip 110 are present.

The reference element 113 may be disposed between the guide element 112 and the index element 114. The reference element 113 may transmit, to the biological analyte monitoring device, a signal associated with the biological analyte generated by the reactor. For example, the reference element 113 may include a reference electrode.

The index element 114 may indicate a target interval in which the biological analyte monitoring device needs to identify a code from the test strip 110.

The second code element 115 may indicate a code at a bit position in the code sequence that is different from a bit position of a code indicated by the first code element 111. The second code element 115 may also indicate whether the test strip 110 is fully inserted in the biological analyte monitoring device. For example, after the test strip 110 is inserted in the biological analyte monitoring device up to the second code element 115 as illustrated in FIG. 1, the biological analyte monitoring device may start measuring the biological analyte injected into the test strip 110.

There is a desire for a blood glucose strip that is competitive in terms of a unit price and is of an improved industrial quality. A variety of correction methods may be applied to the blood glucose strip. For example, a code number may be allocated to a produced blood glucose strip. The biological analyte monitoring device, for example, a blood glucose monitor, may recognize the code number from a code sequence of the blood glucose strip, and correct a measurement result obtained by the blood glucose strip using a correction value corresponding to the code number. Thus, the blood glucose monitor may automatically correct the measurement result based on the code number. For example, when the number of codes included in the code sequence increases, an amount of information to be allocated to the code sequence may also increase, and the blood glucose monitor may thus correct the blood glucose strip with more various characteristics.

Hereinafter, technology for securing a maximum number of codes with a minimum size of area will be described. According to an example embodiment, the test strip 110 may be provided at a cost that is reduced due to less raw materials and higher yields. For more detailed description of the test strip 110 and the biological analyte monitoring device described above with reference to FIG. 1, reference may be made to Korean Patent Registration No. 10-1033649 entitled "biosensor for automatic code sensing and code sensing method using it" and Korean Patent Registration No. 10-1489600 entitled "biosensor for automatic coding."

Hereinafter, a test strip and a biological analyte monitoring device for automatic code recognition will be described in greater detail with reference to the accompanying drawings.

Figure 2:
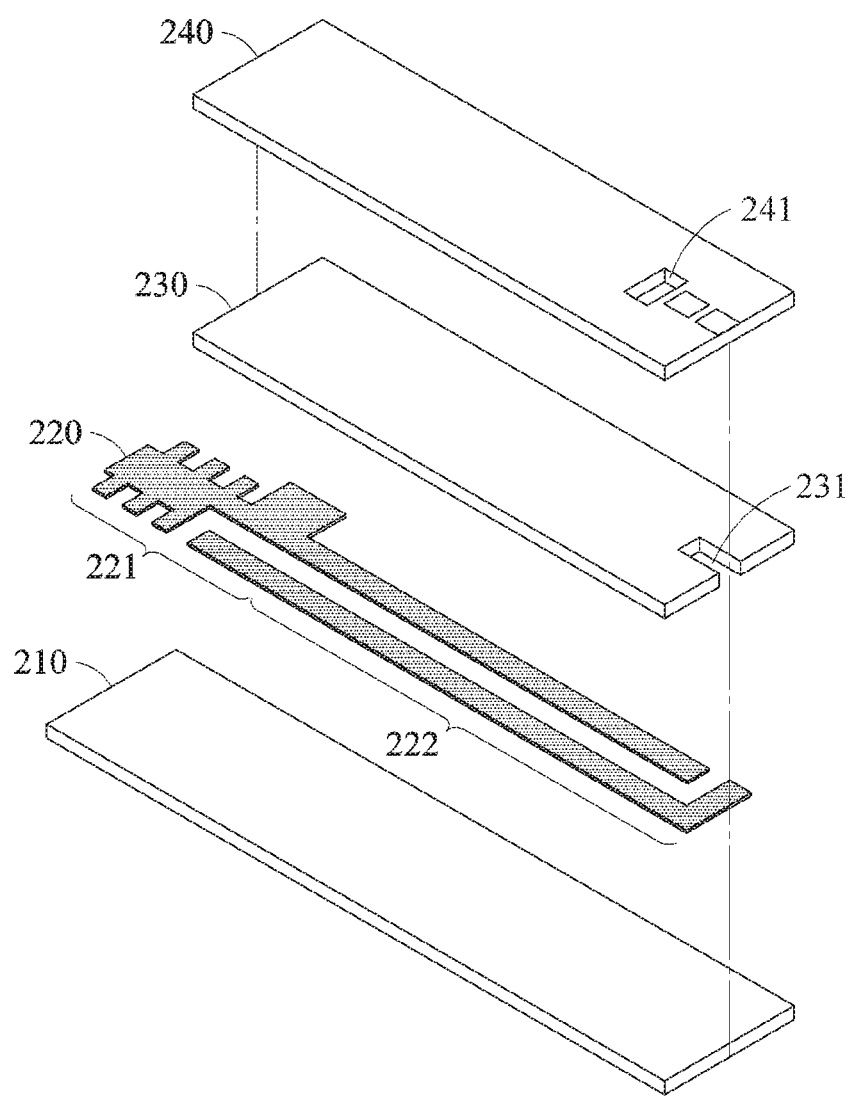
FIG. 2 is a diagram illustrating an example of a layer structure of a test strip according to an example embodiment.

FIG. 2 is a diagram illustrating an example of a layer structure of a test strip according to an example embodiment.

Referring to FIG. 2, a test strip 200 includes a base film 210, an electrode portion 220, a middle layer 230, and a finishing layer 240.

The base film 210 may also be referred to as a substrate film. The base film 210 may be formed on a bottom of the test strip 200 and formed with, for example, a flexible material.

The electrode portion 220 may be disposed on one surface or both surfaces of the base film 210. The electrode portion 220 includes a code indicator 221 and a reactor 222. The electrode portion 220 may be formed with an electrically conductive material, but not limited thereto.

When the test strip 200 is inserted in a strip inserter of a biological analyte monitoring device, the code indicator 221 may indicate a portion being in contact with the strip inserter. The code indicator 221 may indicate a code sequence. The code sequence may be automatically recognized by the biological analyte monitoring device based on, for example, a form of the code indicator 221 and an order in which the code indicator 221 comes into contact with the strip inserter.

The reactor 222 may generate a signal in response to a reaction to a biological analyte. The signal that is generated by the reactor 222 in relation to the biological analyte may be transmitted to the biological analyte monitoring device through the code indicator 221.

The middle layer 230 may include one surface on which an enzyme material or substance is applied and collect the biological analyte. The middle layer 230 includes an inlet 231 on one side thereof into which the biological analyte is injected.

The finishing layer 240 may be provided on the middle layer 230. The finishing layer 240 includes a vent hole 241 to discharge internal air. The vent hole 241 may discharge the internal air when the biological analyte is injected into a position at which the inlet 231 is formed.

A detailed configuration of the test strip 200, for example, a blood glucose strip, may be similar to that described in Korean Patent Registration No. 10-1489600 entitled "biosensor for automatic coding."

Figure 3:
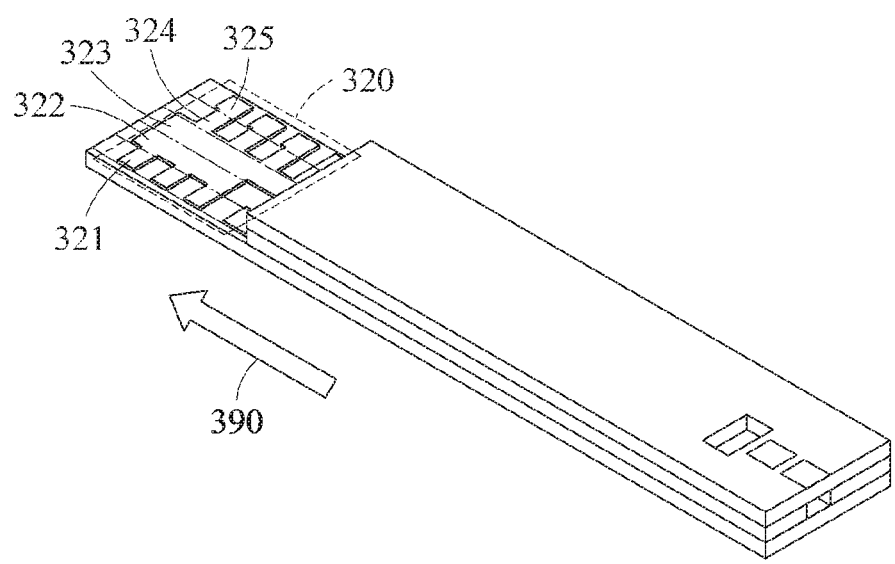
FIG. 3 is a diagram illustrating an example of an electrode portion of a test strip according to an example embodiment.

FIG. 3 is a diagram illustrating an example of an electrode portion of a test strip according to an example embodiment.

Referring to FIG. 3, a test strip 300 includes an electrode portion including a code indicator 320.

As described above, the code indicator 320 may be designed to be a structure that may indicate a code sequence to be automatically recognized by a biological analyte monitoring device while the test strip 300 is being inserted in the biological analyte monitoring device in an insertion direction 390.

The code indicator 320 includes a first code element 321, a guide element 322, a reference element 323, an index element 324, and a second code element 325.

The first code element 321 may indicate a bit value corresponding to at least a portion of codes included in the code sequence. In a case in which the first code element 321 is formed in a certain region, for example, a first element region, the region may indicate a bit value of 1. Conversely, in a case in which the first code element 321 is not formed in the region, the region may indicate a bit value of 0.

The guide element 322 refers to an element that defines a processing interval in which the biological analyte monitoring device needs to process information.

The reference element 323 refers to an element that indicates a reference of a signal. The reference element 323 may be, for example, a reference electrode. For example, the reference element 323 may indicate the ground.

The index element 324 may indicate a target interval. The target interval refers to an interval in which the biological analyte monitoring device needs to identify a code while the test strip 300 is being inserted therein.

The second code element 325 may indicate a bit value corresponding to a remaining portion of the codes in the code sequence. In a case in which the second code element 325 is formed in a certain region, for example, a second element region, the region may indicate a bit value of 1. Conversely, in a case in which the second code element 325 is not formed in the region, the region may indicate a bit value of 0. Herein, the region to which the first code element 321 is allocated, for example, the first element region, and the region to which the second code element 325 is allocated, for example, the second element region, may be distinguished from each other.

In addition, the second code element 325 may indicate a point at which the test strip 300 is fully inserted in the biological analyte monitoring device or a point at which the test strip 300 starts being separated from the biological analyte monitoring device. Thus, the second code element 325 may indicate whether the test strip 300 is completely inserted in the biological analyte monitoring device or not.

Herein, the first code element 321, the guide element 322, the reference element 323, the index element 324, and the second code element 325 may be embodied as an electrode of an electrically conductive material, but not limited thereto. For example, each element may be embodied as an optical element or a mechanical switch element. Thus, the term "element" used herein may be construed as being a broad concept encompassing all elements that may be sensed through physical, chemical, physiochemical, and biochemical methods.

Figure 4:
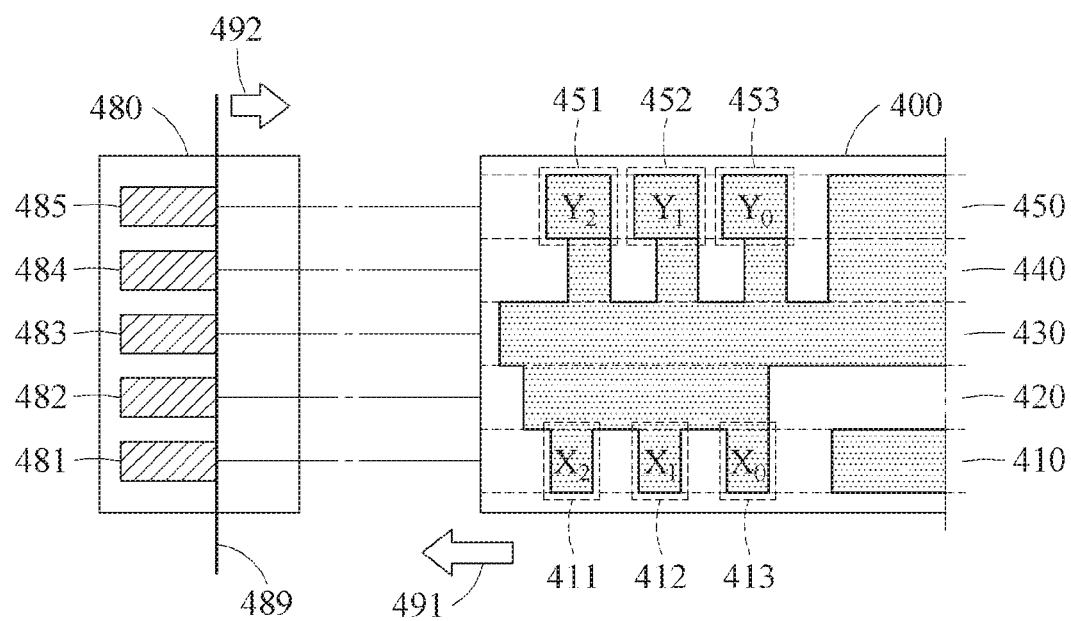
FIG. 4 is a diagram illustrating an example of coupling of an electrode portion of a test strip and a strip inserter of a biological analyte monitoring device according to an example embodiment.

FIG. 4 is a diagram illustrating an example of coupling of an electrode portion of a test strip and a strip inserter of a biological analyte monitoring device according to an example embodiment.

Referring to FIG. 4, an electrode portion of a test strip 400 is divided into a first code region 410, a guide region 420, a reference region 430, an index region 440, and a second code region 450. For example, as illustrated in FIG. 4, each of the first code region 410, the guide region 420, the reference region 430, the index region 440, and the second code region 450 may be elongatedly formed in an insertion direction 491. However, an arrangement of the first code region 410, the guide region 420, the reference region 430, the index region 440, and the second code region 450 is not limited to the example illustrated in FIG. 4, and the arrangement of the regions 410, 420, 430, 440, and 450 may change based on a design.

When the test strip 400 is inserted in a strip inserter 480 of a biological analyte monitoring device, the first code region 410, the guide region 420, the reference region 430, the index region 440, and the second code region 450 may come into contact with pins 481, 482, 483, 484, and 485, respectively, of a detector formed inside the strip inserter 480. Herein, a point at which the pins 481, 482, 483, 484, and 485 formed in the strip inserter 480 are in contact with the electrode portion of the test strip 400 is referred to as a contact point 489. Herein, a proceeding direction 492 in which the contact point 489 proceeds as the test strip 400 is inserted may be opposite to the insertion direction 491.

The biological analyte monitoring device may automatically recognize a code sequence based on such a division of the first code region 410, the guide region 420, the reference region 430, the index region 440, and the second region 450. The code sequence that is automatically recognized by the biological analyte monitoring device may be indicated by an arrangement and a form of each element formed in the first code region 410, the guide region 420, the reference region 430, the index region 440, and the second code region 450. The biological analyte monitoring device may collect and process information from each of the regions 410, 420, 430, 440, and 450 while the test strip 400 is being inserted in the biological analyte monitoring device.

The first code region 410 may be a region corresponding to at least a portion of codes in the code sequence. As illustrated, the first code region 410 includes a plurality of first element regions 411, 412, and 413. Each of the first element regions 411, 412, and 413 may correspond to one code among the at least a portion of the codes in the code sequence. For example, in a case in which a first code element is formed in a first element region among the first element regions 411, 412, and 413, a code corresponding to the first element region may indicate a bit value of 1. Also, in a case in which the first code element is not formed in a first element region among the first element regions 411, 412, and 413, a code corresponding to the first element region may indicate a bit value of 0.

The second code region 450 may be a region corresponding to a remaining portion of the codes in the code sequence. As illustrated, the second code region 450 includes a plurality of second element regions 451, 452, and 453. Each of the second element regions 451, 452, and 453 of the second code region 450 may correspond to one code among the remaining portion of the codes in the code sequence. For example, in a case in which a second code element is formed in a second element region among the second element regions 451, 452, and 453, a code corresponding to the second element region may indicate a bit value of 1. Also, in a case in which the second code element is not formed in a second element region among the second element regions 451, 452, and 453, a code corresponding to the second element region may indicate a bit value of 0.

In an example, a code element may be formed or not be formed in each of the first element regions 411, 412, and 413, and the second element regions 451, 452, and 453, based on the code sequence. For example, a code indicated by each element region is illustrated as X or Y in FIG. 4. For example, as illustrated, the first element regions 411, 412, and 413 indicate codes $X_2$, $X_1$, and $X_0$, respectively, and the second element regions 451, 452, and 453 indicate codes $Y_2$, $Y_1$, and $Y_0$, respectively. The codes $X_2$, $X_1$, $X_0$, $Y_2$, $Y_1$, and $Y_0$ may indicate a bit value of 1 or 0 based on whether a code element is formed or not. Thus, the code sequence indicated by the first code region 410 and the second code region 450 may indicate a binary number of $Y_2Y_1Y_0X_2X_1X_0$, which may be decimally represented as $Y_2 \cdot 2^5 + Y_1 \cdot 2^4 + Y_0 \cdot 2^3 + X_2 \cdot 2^2 + X_1 \cdot 2^1 + X_0 \cdot 2^0$. However, the number of the codes included in the code sequence is not limited to the example described in the foregoing and may change based on a design. For example, the number of codes in the code sequence may be defined by the number of index elements included in the index region 440. For example, in a case in which there are m index elements, the number of codes in the code sequence may be 2m, wherein m denotes an integer greater than or equal to 1. In this example, the code sequence indicated by the first code region 410 and the second code region 450 may indicate binary number of $X_2X_1X_0Y_2Y_1Y_0$, which may be decimally represented as $X_2 \cdot 2^5 + X_1 \cdot 2^4 + X_0 \cdot 2^3 + Y_2 \cdot 2^2 + Y_1 \cdot 2^1 + Y_0 \cdot 2^0$.

The index region 440 may include a plurality of index elements. An interval in an index element is formed the index region 440 may indicate a target interval in which a code may be formed. For example, in the index region 440 defined elongatedly in the insertion direction 491, a position of each of the index elements on an axis parallel to the insertion direction 491 may correspond to a position of each of the first element regions 411, 412, and 413 and a position of each of the second element regions 451, 452, and 453.

The guide region 420 may be a region in which a guide element is disposed. As described above, the guide element may indicate a processing interval in which the code sequence is recognized.

The reference region 430 may be a region in which a reference element is disposed. The reference element may be connected up to a reactor of the test strip 400.

The first element regions 411, 412, and 413 may indicate a code corresponding to a first bit position, and the second element regions 451, 452, and 453 may indicate a code corresponding to a second bit position different from the first bit position. For example, the first bit position may be lower than the second bit position. However, the positions are not limited to the example described in the foregoing, and they may be designed conversely. For example, in a case in which the number of the index elements is m, the first element regions 411, 412, and 413 may indicate m−1th through 0th bit positions in the code sequence based on an order in which each of the first element regions 411, 412, and 413 comes into contact with the biological analyte monitoring device while the test strip 400 is being inserted in the biological analyte monitoring device. Also, the second element regions 451, 452, and 453 may indicate 2m−1th through mth bit positions in the code sequence based on an order in which each of the second element regions 451, 452, and 453 comes into contact with the biological analyte monitoring device while the test strip 400 is being inserted in the biological analyte monitoring device. Herein, m denotes an integer greater than or equal to 1.

Hereinafter, how the biological analyte monitoring device automatically recognizes the code sequence from the test strip 400 while the test strip 400 is being inserted in the biological analyte monitoring device will be described in detail with reference to FIGS. 6 through 12.

Figure 5:
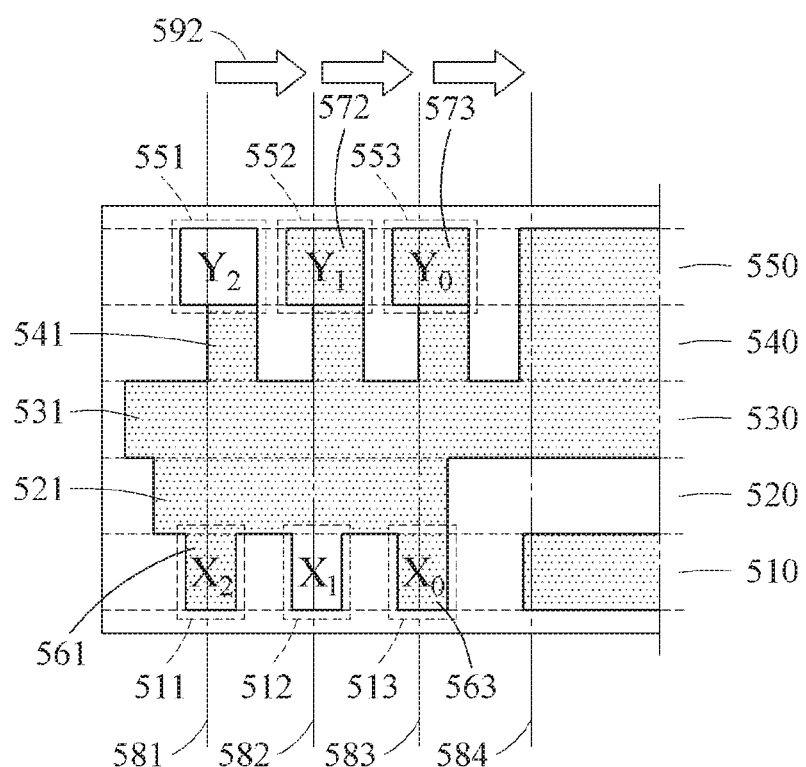
FIG. 5 is a diagram illustrating a detailed example of an electrode portion of a test strip according to an example embodiment.

FIG. 5 is a diagram illustrating a detailed example of an electrode portion of a test strip according to an example embodiment.

FIG. 5 illustrates an example of the electrode portion of the test strip 400 described above with reference to FIG. 4. Referring to FIG. 5, similarly to the example illustrated in FIG. 4, an electrode portion of a test strip 500 is divided into a first code region 510, a guide region 520, a reference region 530, an index region 540, and a second code region 550.

The first code region 510 includes a plurality of first element regions 511, 512, and 513. In the example illustrated in FIG. 5, first code elements 561 and 563 are formed in some of the first element regions 511, 512, and 513, for example, the first element region 511 and the first element region 513. The first element regions 511, 512, and 513 are disposed separately from each other along an insertion direction. Herein, a front end of each of the first element regions 511, 512, and 513 may be disposed ahead of a front end of a corresponding index element among a plurality of index elements 541, in the insertion direction.

The second code region 550 includes a plurality of second element regions 551, 552, and 553. In the example illustrated in FIG. 5, second code elements 572 and 573 are formed in some of the second element regions 551, 552, and 553, for example, the second element region 552 and the second element region 553. The second element regions 551, 552, and 553 are disposed separately from each other along the insertion direction. Herein, a front end of each of the second element regions 551, 552, and 553 may be disposed ahead of a front end of a corresponding index element among the index elements 541, in the insertion direction.

As described, the test strip 500 may include at least one code element that may be formed in the first element regions 511, 512, and 513 and the second element regions 551, 552, and 553. However, examples are not limited to the illustrated example, and the code element may not be formed in the test strip 500 and a code sequence may indicate 0 in such an example.

The guide region 520 includes a guide element 521 that is elongatedly formed in the insertion direction. The guide element 521 is disposed in parallel with a reference element 531 along the insertion direction and may indicate a processing interval for the code sequence indicating information associated with the test strip 500.

The reference region 530 includes the reference element 531 that is elongatedly formed in the insertion direction. The guide element 521 and the reference element 531 are mutually connected. A front end of the reference element 531 may be disposed ahead of a front end of the guide element 521 in the insertion direction. A portion of the reference element 531 may be connected to the index elements 541.

The index region 540 includes the index elements 541. Each of the index elements 541 is connected to the reference element 531. The index elements 541 are disposed separately from each other along the insertion direction. In an example, each of the index elements 541 may overlap at least a portion of a first element region corresponding to a corresponding index element among the first element regions 511, 512, and 513 and at least a portion of a second element region corresponding to a corresponding index element among the second element regions 551, 552, and 553, in a direction vertical to the insertion direction.

As illustrated, contact points 581, 582, 583, and 584 at which the test strip 500 and the biological analyte monitoring device come in contact with each other may proceed in a proceeding direction 592 in which the test strip 500 proceeds while being inserted. As the contact points 581, 582, 583, and 584 proceed, the biological analyte monitoring device may sequentially recognize codes in the code sequence.

For example, at least a portion of the reference element 531, at least a portion of the index elements 541, and at least a portion of the guide element 521 may overlap one another to be connected in the direction vertical to the insertion direction. Thus, the reference element 531, the index elements 541, and the guide element 521 may be connected at each of the contact points 581, 582, and 583 in the processing interval. The biological analyte monitoring device may determine, to be a target interval, an interval in which the reference element 531, the index elements 541, and the guide element 521 are connected, and identify a code in each target interval.

In addition, the second code region 550 also includes an insertion completion indicator that is disposed separately from the second element regions 551, 552, and 553 along the insertion direction and is also disposed by being disconnected from the guide element 521 indicating the processing interval for the code sequence. The insertion completion indicator may be a second code element disposed in the second code region 550, passing the processing interval.

The biological analyte monitoring device may identify codes of $X_2$ and $Y_2$ at the first contact point 581. The biological analyte monitoring device may also identify codes of $X_1$ and $Y_1$ at the second contact point 582. The biological analyte monitoring device may also identify codes of $X_0$ and $Y_0$ at the third contact point 583. The biological analyte monitoring device may determine whether to terminate the insertion at the fourth contact point 584. The test strip 500 may indicate a binary number of $Y_2Y_1Y_0X_2X_1X_0=011101$, which may also be decimally represented as $0 \cdot 2^5 + 1 \cdot 2^4 + 1 \cdot 2^3 + 1 \cdot 2^2 + 0 \cdot 2^1 + 1 \cdot 2^0 = 0 + 16 + 8 + 4 + 0 + 1 = 29$. Hereinafter, an operation at each contact point will be described in greater detail with reference to FIGS. 6 through 12.

FIGS. 6 through 12 are diagrams illustrating an example of how a biological analyte monitoring device automatically recognizes a code while a test strip is being inserted in the biological analyte monitoring device according to an example embodiment.

Figure 6:
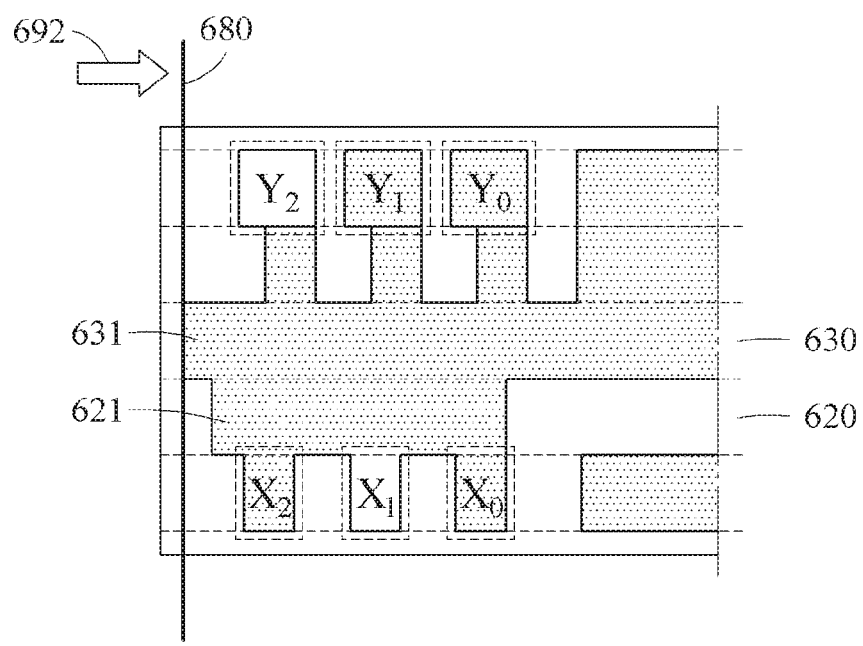
FIGS. 6 through 12 are diagrams illustrating an example of how a biological analyte monitoring device automatically recognizes a code while a test strip is being inserted therein according to an example embodiment.

FIG. 6 illustrates an example of when a contact point 680 between a strip inserter of a biological analyte monitoring device and a test strip 600 reaches a reference element 631 of a reference region 630 in a proceeding direction 692. For example, as illustrated, a portion of the reference element 631 is disposed ahead of a guide element 621 of a guide region 620 in an insertion direction. Thus, the biological analyte monitoring device may come into contact with the reference element 631 before coming into contact with the guide element 621, while the test strip 600 is being inserted in the biological analyte monitoring device. The biological analyte monitoring device may apply a signal to the reference element 631 being in contact first, and thus rapidly stabilize the signal applied to the reference element 631.

Figure 7:
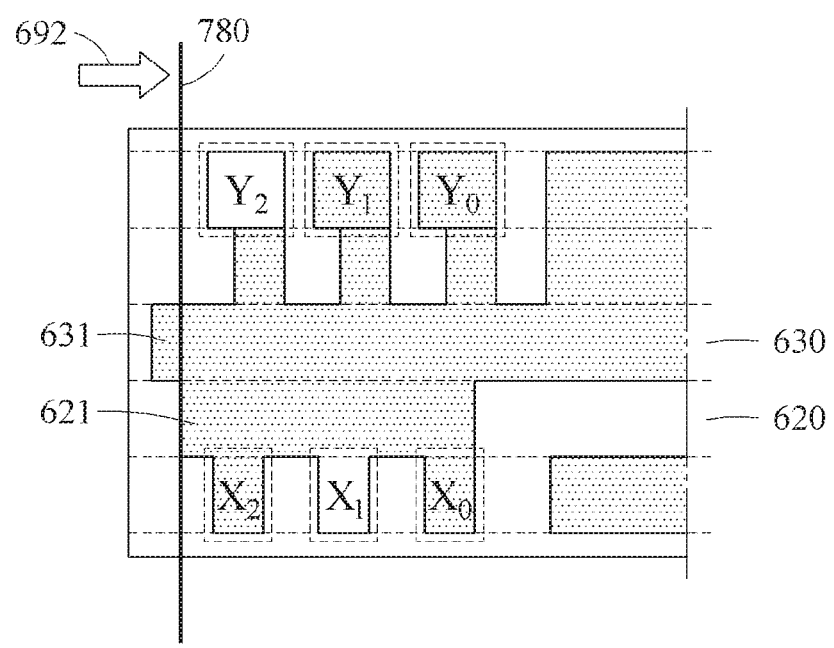

FIG. 7 illustrates an example of when a contact point 780 between the strip inserter and the test strip 600 reaches the guide element 621 of the guide region 620 in the proceeding direction 692. In an example, the biological analyte monitoring device may verify whether the reference element 631 and the guide element 621 are connected to each other. For example, the biological analyte monitoring device may apply a signal to the guide element 621 and detect a signal path formed between the reference element 631 and the guide element 621. When the reference element 631 and the guide element 621 are verified to be connected to each other, the biological analyte monitoring device may determine that the contact point 780 is currently being in a processing interval.

Figure 8:
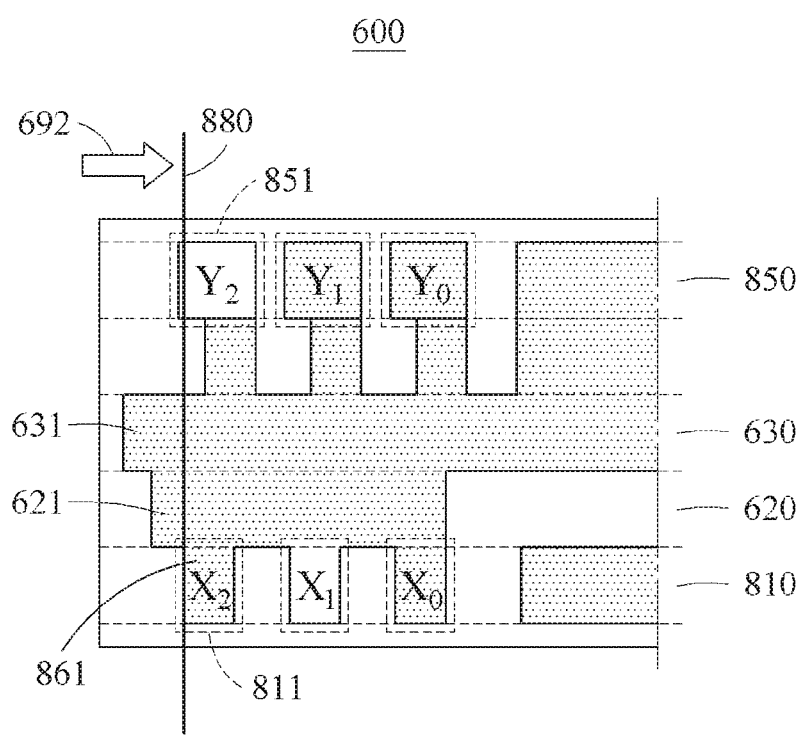

FIG. 8 illustrates an example of when a contact point 880 reaches a first element region 811 of a first code region 810 and a second element region 851 of a second code region 850 in the proceeding direction 692. For example, as illustrated, at least a portion of the first element region 811 and at least a portion of the second element region 851 may be formed ahead of an index element in the insertion direction. The biological analyte monitoring device may apply a signal to the first element region 811 and the second element region 851 before applying a signal to the index element, and thus stabilize the signal applied to the first element region 811 and the second element region 851. That is, the biological analyte monitoring device may stabilize the signal applied to the first element region 811 and the second element region 851 before a target interval indicated by the index element. As illustrated, a first code element 861 is formed only in the first element region 811, and the biological analyte monitoring device may thus apply the signal to the first code element 861.

Figure 9:
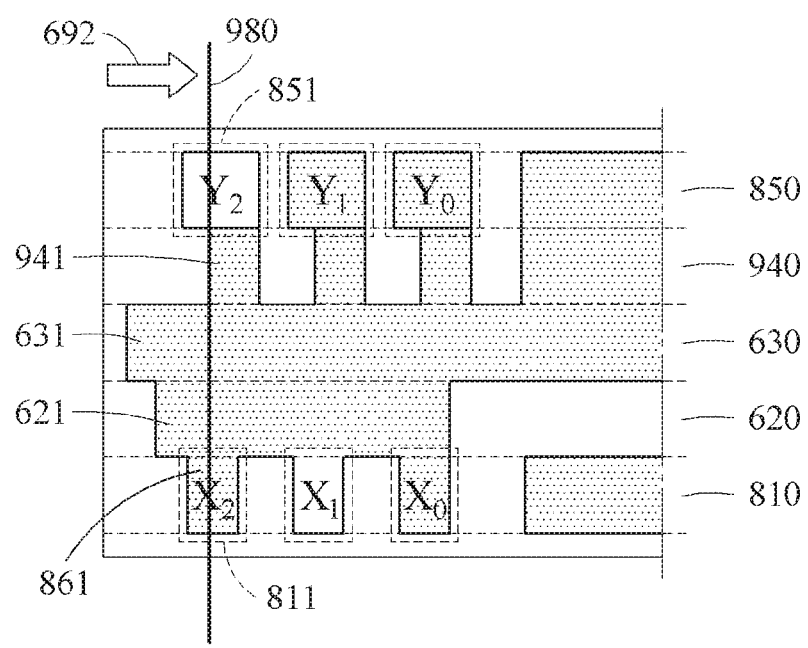

FIG. 9 illustrates an example of when a contact point 980 reaches an index element 941 of an index region 940 in the proceeding direction 692. In an example, the biological analyte monitoring device may verify whether each code element is connected, directly or indirectly, to the reference element 631. For example, the biological analyte monitoring device may apply a signal to each code element and detect a signal path formed among code elements, for example, the first code element 861, the index element 941, the guide element 621, and the reference element 631. For example, the biological analyte monitoring device may determine a code corresponding to the first element region 811 to be a bit value of 1 because the first code element 861 that is connected to the index element 941, the guide element 621, and the reference element 631 is formed. In addition, the biological analyte monitoring device may determine a code corresponding to the second element region 851 to be a bit value of 0 because a second code element that is connected to the index element 941, the guide element 621, and the reference element 631 is not formed. Referring back to FIG. 8, the signal is already applied to the first element region 811 and the second element region 851, and thus the biological analyte monitoring device may detect a stabilized signal from each code element.

Figure 10:
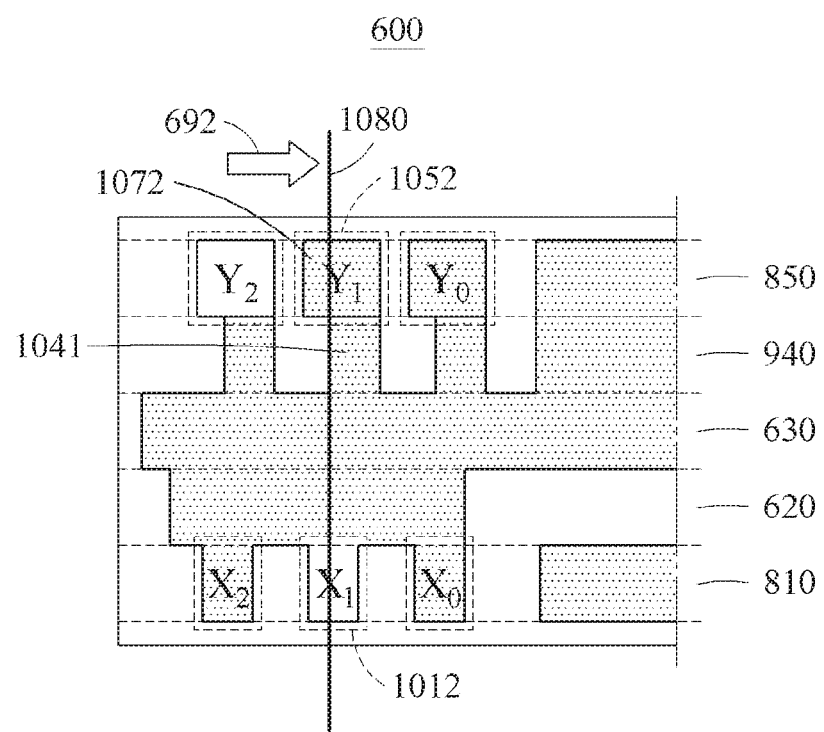

FIG. 10 illustrates an example of when a contact point 1080 reaches a subsequent index element 1041 in the proceeding direction 692. As described above, the biological analyte monitoring device may determine whether each code element is connected to a remaining element. In the example illustrated in FIG. 10, the biological analyte monitoring device may determine a code corresponding to a first element region 1012 to be a bit value of 0 because a first code element is not detected from the first element region 1012. In addition, the biological analyte monitoring device may determine a code corresponding to a second element region 1052 to be a bit value of 1 because a second code element 1072 is detected from the second element region 1052.

Figure 11:
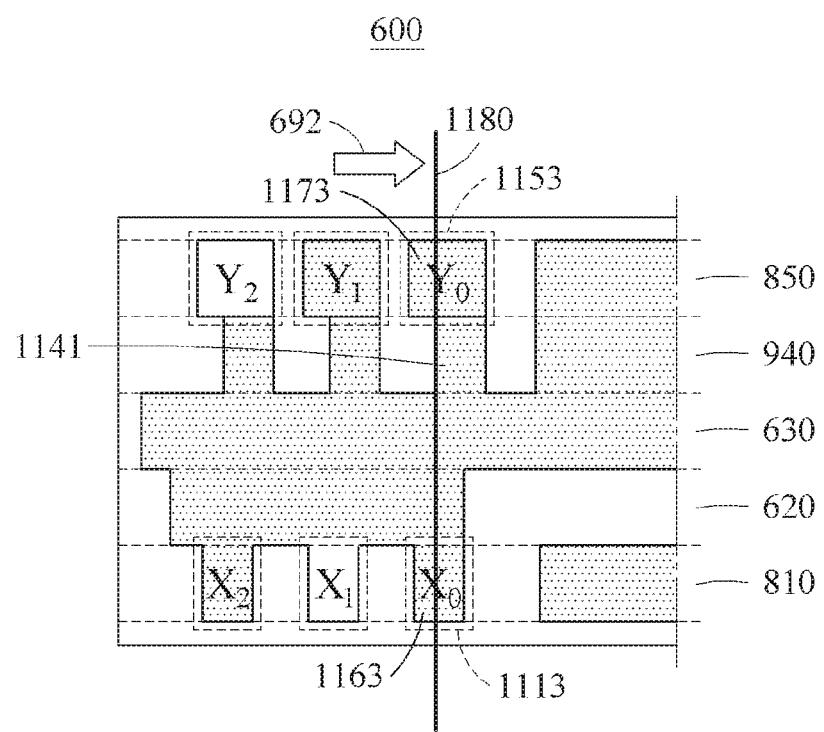

FIG. 11 illustrates an example of when a contact point 1180 reaches a subsequent index element 1141 in the proceeding direction 692. In the example illustrated in FIG. 11, the biological analyte monitoring device may detect a first code element 1163 from a first element region 1113 and a second code element 1173 from a second element region 1153. Thus, the biological analyte monitoring device may determine, to be a bit value of 1, a code corresponding to each of the first element region 1113 and the second element region 1153 and indicated by the corresponding index element 1141.

As described above, when codes of $Y_2$, $Y_1$, $Y_0$, $X_2$, $X_1$, and $X_0$ are arranged in sequential order to be a binary number, a code sequence may be represented as the binary number of 011101. The biological analyte monitoring device may recognize a decimal number, for example, 0+16+8+4+0+1=29, which is obtained through conversion from the binary number 011101.

Although not illustrated in FIGS. 6 through 11, when a path from each code element to a reference element based on a contact point is isolated, despite a code element being formed, the biological analyte monitoring device may identify, to be a bit value of 0, a code corresponding to a corresponding element region.

Figure 12:
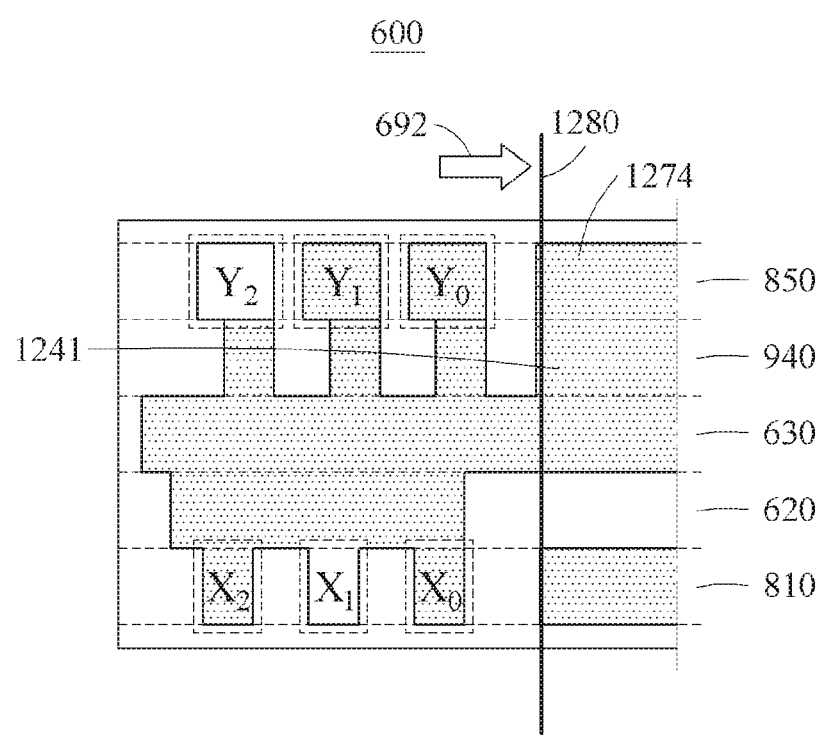

FIG. 12 illustrates an example of when a contact point 1280 reaches a subsequent index element 1241 in the proceeding direction 692. While the test strip 600 is proceeding from as shown in the example illustrated in FIG. 11 to as shown in the example illustrated in FIG. 12, the biological analyte monitoring device may detect that a connection between a reference element and a guide element is released. The biological analyte monitoring device may terminate recognition of a code sequence because a processing interval is terminated. When a second code element 1274 is detected after the connection between the reference element and the guide element is released, the biological analyte monitoring device may determine that insertion of the test strip 600 is completed. For example, the biological analyte monitoring device may determine whether a signal path between the second code element 1274 and the reference element is formed.

According to an example embodiment, when insertion of a test strip is completed, the biological analyte monitoring device may receive a measurement initiation command from the test strip. The biological analyte monitoring device may terminate recognition of a code sequence, and then start measuring an amount of a biological analyte from the test strip.

Although it is illustrated in FIG. 12 that the index element 1241 is formed in the index region 940, examples are not limited to the illustrated example. For example, the index element 1241 may not be formed in the index region 940 in an interval after the connection between the reference element and the guide element is released. In such an example, the biological analyte monitoring device may detect whether the second code element 1274 is formed, while excluding detection of the index element 1241, after the connection between the reference element and the guide element is released by the insertion of the test strip 600.

In addition, the index region 940 in the interval after the connection between the reference element and the guide element is released may indicate an additional bit of the code sequence. In an example, the index region 940 in the internal may indicate a bit at a highest bit position of the code sequence or a lowest bit position of the code sequence. For example, in the interval, the index region 940 may indicate a 2mth bit position, and the second code region 850 may indicate 2m−1th through mth bit positions and the first code region 810 may indicate m−1th through 0th bit positions. For another example, in the interval, the index region 940 may indicate a 0th bit position, and the second code region 850 may indicate 2mth through m+1th bit positions and the first code region 810 may indicate mth through 1st bit positions. When the index element 1241 is formed in the index region 940 in the interval, a bit value of the additional bit may indicate 1. Conversely, when the index element 1241 is not formed in the index region 940 in the interval, a bit value of the additional bit may indicate 0.

Figure 13:
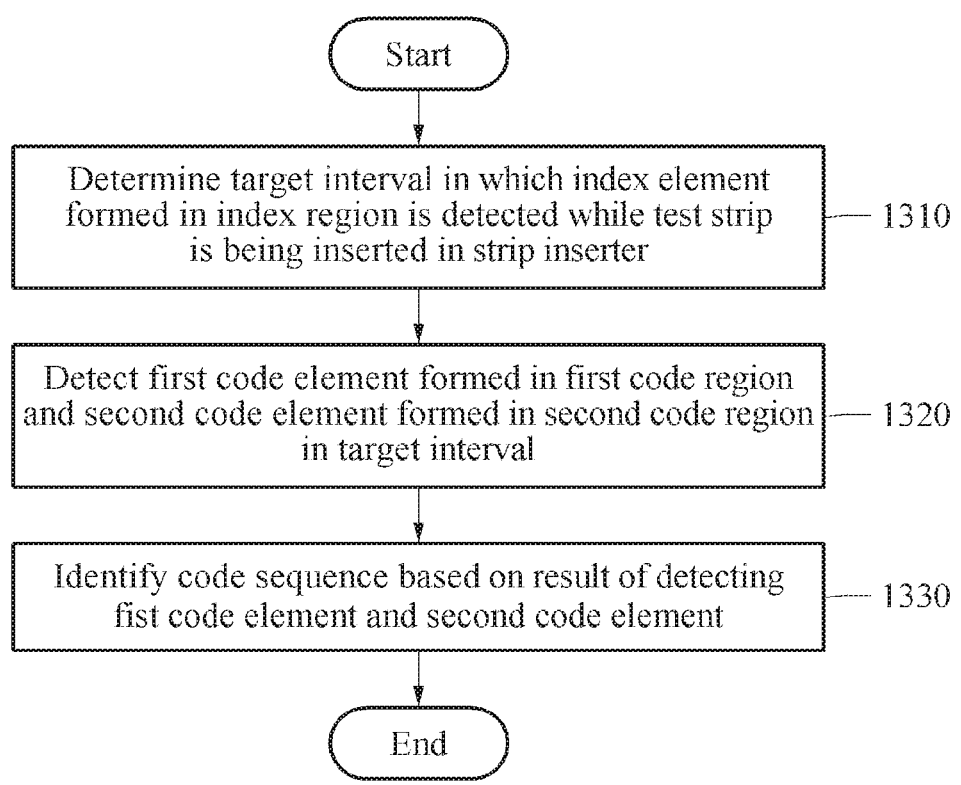
FIG. 13 is a flowchart illustrating an example of a method of automatically recognizing a code by a biological analyte monitoring device according to an example embodiment.

FIG. 13 is a flowchart illustrating an example of a method of automatically recognizing a code by a biological analyte monitoring device according to an example embodiment.

Referring to FIG. 13, in operation 1310, the biological analyte monitoring device determines a target interval in which an index element formed in an index region is detected while a test strip is being inserted in a strip inserter of the biological analyte monitoring device. For example, the biological analyte monitoring device may determine whether a connection between the index element and a reference element is formed.

In operation 1320, the biological analyte monitoring device detects a first code element formed in a first code region and a second code element formed in a second code region, in the target interval. For example, the biological analyte monitoring device may determine whether the first code element is connected to the reference element during the target interval, and also determine whether the second code element is connected to the reference element during the target interval.

In operation 1330, the biological analyte monitoring device identifies a code sequence based on a result of detecting the first code element and the second code element. For example, when a code element is detected in the target interval, the biological analyte monitoring device may determine a code corresponding to the target interval to be a bit value of 1. For another example, the biological analyte monitoring device may determine, to be a bit value of 0, a code corresponding to an element region from which a code element is not detected during the target interval. The biological analyte monitoring device may arrange codes identified in sequential order and recognize the code sequence indicated by the test strip.

An automatic code recognizing method is not limited to the method described above with reference to FIG. 13. Thus, the method may be performed along with the operations described above with reference to FIGS. 1 through 12. In addition, an order of the operations described above with reference to FIG. 13 is not limited to the order described, and thus the order may change, and some operations may be omitted or added based on a design.

Figure 14:
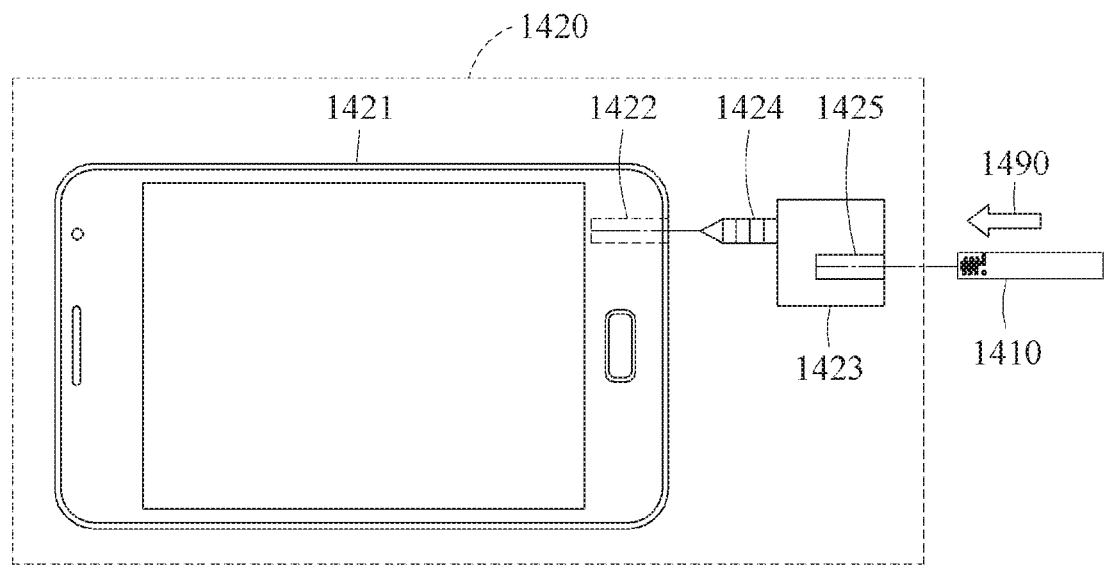
FIG. 14 is a diagram illustrating an example of a biological analyte monitoring device according to an example embodiment.

FIG. 14 is a diagram illustrating an example of a biological analyte monitoring device according to an example embodiment.

Referring to FIG. 14, a biological analyte monitoring system 1400 includes a test strip 1410 and a biological analyte monitoring device 1420.

As illustrated, the test strip 1410 may be inserted in the biological analyte monitoring device 1420 in an insertion direction 1490. For a detailed configuration of the test strip 1410, reference may be made to the related descriptions provided above.

Herein, the biological analyte monitoring device 1420 may be a device in which a biological analyte analyzer 1421 and a biological analyte measuring module 1423 are combined. The biological analyte analyzer 1421 and the biological analyte measuring module 1423 may be combined through a socket 1422 and a plug 1424. The test strip 1410 may be inserted in a strip inserter 1425 of the biological analyte measuring module 1423. However, the biological analyte monitoring device 1420 is not limited to a form in which two modules are combined as illustrated.

Figure 15:
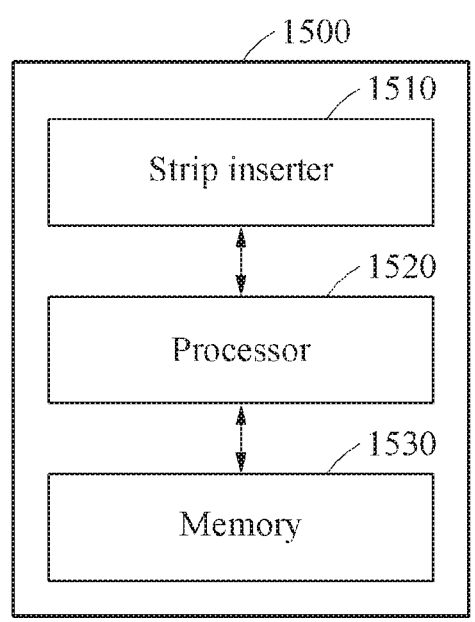
FIGS. 15 and 16 are diagrams illustrating examples of a configuration of a biological analyte monitoring device according to an example embodiment.
Figure 16:
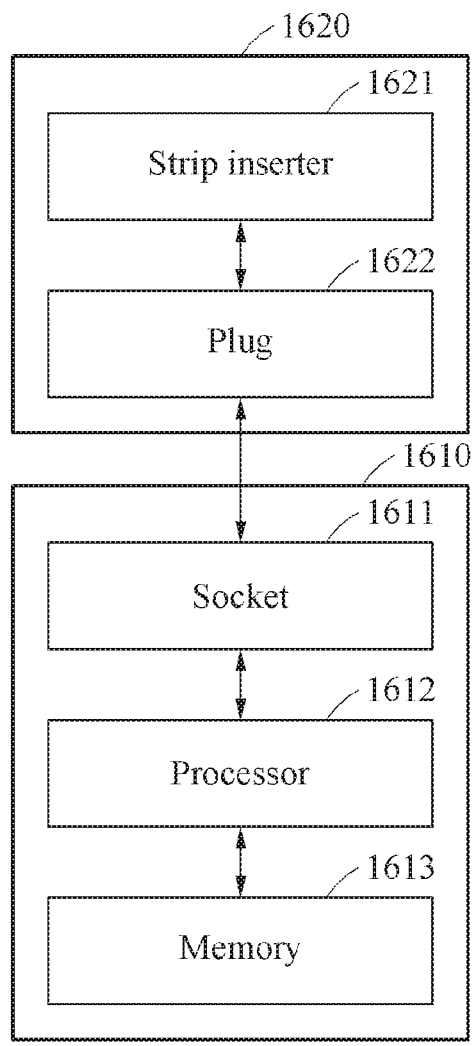

FIGS. 15 and 16 are diagrams illustrating examples of a configuration of a biological analyte monitoring device according to an example embodiment.

Referring to FIG. 15, a biological analyte monitoring device includes a strip inserter 1510, a processor 1520, and a memory 1530.

The strip inserter 1510 refers to an inlet portion in which a test strip is to be inserted. For example, the strip inserter 1510 may be embodied in a form of a socket including a plurality of pins, for example, five pins.

In response to the test strip being inserted in the strip inserter 1510, the processor 1520 may recognize or read a code sequence based on an element detected from an index region, a first code region, and a second code region of the test strip.

The processor 1520 may determine a target interval in which an index element formed in the index region is detected while the test strip is being inserted in the strip inserter 1510. The processor 1520 may detect a first code element formed in the first code region and a second code element formed in the second code region, in the target interval. The processor 1520 may identify the code sequence based on a result of detecting the first code element and the second code element.

For example, in response to the first code element being detected from the first code region during the target interval, the processor 1520 may determine, to be 1, a code in the code sequence corresponding to the first code region in the target interval. Conversely, in response to the first code element not being detected from the first code region during the target interval, the processor 1520 may determine, to be 0, a code in the code sequence corresponding to the first code region in the target interval. Also, in response to the second code element being detected from the second code region during the target interval, the processor 1520 may determine, to be 1, a code in the code sequence corresponding to the second code region in the target interval. Conversely, in response to the second code element not being detected in the second code region in the target interval, the processor 1520 may determine, to be 0, a code in the code sequence corresponding to the second code region in the target interval.

In addition, the processor 1520 may allocate a first bit position to the code identified from the first code region. The processor 1520 may also allocate a second bit position different from the first bit position to the code identified from the second code region. A bit position used herein may indicate a specified number of digits occupied by a corresponding code in the code sequence.

The processor 1520 may determine a plurality of target intervals in sequential order while the test strip is being inserted in the strip inserter 1510. The processor 1520 may identify a plurality of first codes corresponding to the first code region in the respective target intervals, and a plurality of second codes corresponding to the second code region in the respective target intervals. The processor 1520 may allocate, to the second codes, a bit position different from a bit position allocated to the first codes.

For example, in response to m index elements being detected, the processor 1520 may determine m target intervals in sequential order. The processor 1520 may allocate 2m−1th through mth bit positions to the second code region. The processor 1520 may also allocate m−1th through 0th bit positions to the first code region. Herein, m denotes an integer greater than or equal to 1.

In response to a contact between the second code element and the strip inserter 1510 being detected, the processor 1520 may apply a signal to the second code element. After an entry into the target interval, the processor 1520 may detect a code element from the first code region and the second code region.

The processor 1520 may determine a processing interval in which a reference element formed in a reference region and a guide element formed in a guide region are connected. The processor 1520 may determine, to be the target interval, an interval in which an index element connected to the reference element and the guide element is detected in the processing interval. In response to a signal path from the first code region to the reference region being detected in the target interval, the processor 1520 may determine that the first code element is formed in the first code region. In response to ta signal path from the second code region to the reference region being detected in the target interval, the processor 1520 may determine that the second code element is formed in the second code region.

In response to a contact between the strip inserter 1510 and the first code element being detected in the target interval, the processor 1520 may apply a signal to the first code element. In response to the applied signal reaching the reference element, the processor 1520 may determine that the first code element is formed. Similarly, in response to a contact between the strip inserter 1510 and the second code element being detected in the target interval, the processor 1520 may apply a signal to the second code element. In response to the applied signal reaching the reference element, the processor 1520 may determine that the second code element is formed.

In response to the connection between the reference element and the guide element being released, the processor 1520 may terminate the recognizing or the reading of the code sequence. For example, when a connection between the second code element and the reference element is detected after the connection between the reference element and the guide element is released, the processor 1520 may determine that the test strip is completely inserted.

The operations of the processor 1520 are not limited to the operations described above with reference to FIG. 15, and the processor 1520 may perform one or more or all operations described above with reference to FIGS. 1 through 14.

The memory 1530 may store, temporarily or permanently, data required for automatic code recognition. For example, the memory 1530 may store a list of correction values corresponding to a code number indicated by the code sequence. In addition, the memory 1530 may store one or more programs including instructions to perform operations for the automatic code recognition.

Referring to FIG. 16, a biological analyte analyzer 1610 and a biological analyte measuring module 1620 are combined in a biological analyte monitoring device.

The biological analyte analyzer 1610 includes a processor 1612 and a memory 1613, which are embodied similarly to the processor 1520 and the memory 1530 described above with reference to FIG. 15. The biological analyte analyzer 1610 may be embodied as a smart device, such as, for example, a smartphone, and may further include a display to display a result of measuring a blood glucose level and a power supply to supply power. The biological analyte analyzer 1610 also includes a socket 1611 to be connected to a plug 1622 of the biological analyte measuring module 1620. The socket 1611 may be, for example, a microphone socket, but not limited to the example.

The biological analyte measuring module 1620 includes a strip inserter 1621 that may be embodied as a socket including a plurality of pins as described above. The plug 1622 may be embodied as, for example, a phone jack plug, but not limited to the example.

According to example embodiments described herein, a blood glucose strip for automatic code recognition may obtain a maximum number of codes only with a minimum size of area.

The blood glucose strip may be produced with a reduced amount of raw materials.

Further, the blood glucose strip may also be produced at an increased yield, and thus provided at a reduced cost.

The example embodiments described herein relates to a blood glucose strip for automatic code recognition, and more particularly, to a blood glucose strip for automatic code recognition that may obtain a maximum number of codes with a minimum size of area.

The devices, units, components, and/or portions described herein may be implemented using hardware components and software components. For example, the hardware components may include microphones, amplifiers, band-pass filters, audio to digital convertors, non-transitory computer memory and processing devices. A processing device may be implemented using one or more general-purpose or special purpose computers, such as, for example, a processor, a controller, an application specific integrated circuit (ASIC), an arithmetic logic unit, a digital signal processor (DSP), a microcomputer, a field programmable gate array (FPGA), a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A test strip comprising:
   a base film;
   an electrode portion disposed on one surface of the base film; and
   a layer of which one surface is applied with an enzyme substance, and formed on at least a portion of a top surface of the electrode portion to collect a biological analyte,
   wherein the electrode portion comprises:
   a reference element elongatedly formed in an insertion direction in which the test strip is inserted in a biological analyte monitoring device;
   a plurality of first element regions disposed separately from each other along the insertion direction, wherein the plurality of first element regions includes a first element region that is disposed sequentially first along the insertion direction;
   a plurality of second element regions disposed separately from each other along the insertion direction, wherein the plurality of second element regions includes a second element region that is disposed sequentially first along the insertion direction; and
   a plurality of index elements disposed separately from each other along the insertion direction, wherein the plurality of index elements includes an index element that is disposed sequentially first along the insertion direction;
   wherein at least a portion of the first element region and at least a portion of the second element region are disposed ahead of the index element relative to the insertion direction;
   wherein the index element is arranged between the first and second element regions; and
   wherein each of the index elements overlaps at least a portion of a first element region corresponding to a corresponding index element among the first element regions, and at least a portion of a second element region corresponding to a corresponding index element among the second element regions, in a direction vertical to the insertion direction.

2. The test strip of claim 1, further comprising:
   a guide element disposed in parallel with the reference element in the insertion direction and configured to indicate a processing interval for a code sequence indicating information associated with the test strip.

3. The test strip of claim 2, wherein a front end of the reference element is disposed ahead of a front end of the guide element in the insertion direction.

4. The test strip of claim 1, wherein a code element is formed or not formed in the first element regions and the second element regions based on a code sequence.

5. The test strip of claim 1, wherein a front end of each of the second element regions is disposed ahead of a front end of a corresponding index element among the index elements in the insertion direction.

6. The test strip of claim 1, wherein a front end of each of the first element regions is disposed ahead of a front end of a corresponding index element among the index elements in the insertion direction.

7. The test strip of claim 1, further comprising:
   a guide element disposed in parallel with the reference element in the insertion direction,
   wherein at least a portion of the reference element, at least a portion of the index elements, and at least a portion of the guide element overlap to be connected in a direction vertical to the insertion direction.

8. The test strip of claim 1, comprising:
   an insertion completion indicator disposed separately from the second element regions in the insertion direction, disposed by being disconnected from a guide element indicating a processing interval for a code sequence, and disposed in a second code region including the second element regions.

9. The test strip of claim 1, wherein the first element regions indicate a code corresponding to a first bit position, and
   the second element regions indicate a code corresponding to a second bit position different from the first bit position.

10. The test strip of claim 1, wherein, when a number of the index elements is m,
    the second element regions indicate 2m−1th through mth bit positions in a code sequence based on an order in which each of the second element regions comes into contact with the biological analyte monitoring device while the test strip is being inserted in the biological analyte monitoring device, and
    the first element regions indicate m−1th through 0th bit positions in the code sequence based on an order in which each of the first element regions comes into contact with the biological analyte monitoring device while the test strip is being inserted in the biological analyte monitoring device,
    wherein m denotes an integer greater than or equal to 1.

* * * * *